United States Patent [19]
Jaffe et al.

[11] Patent Number: 5,364,404
[45] Date of Patent: Nov. 15, 1994

[54] NEODYMIUM-BASED MAGNETIC RETRIEVAL CATHETER

[75] Inventors: Richard B. Jaffe, Salt Lake City, Utah; Frank A. Parrish, Ellettsville, Ind.

[73] Assignee: Cook Incorporated, Bloomington, Ind.

[21] Appl. No.: 940,765

[22] Filed: Sep. 4, 1992

Related U.S. Application Data

[63] Continuation of Ser. No. 632,336, Dec. 21, 1990, abandoned.

[51] Int. Cl.⁵ .............................................. A61B 17/52
[52] U.S. Cl. ................................................... 606/106
[58] Field of Search ............................ 600/11; 606/106; 604/264, 280, 270

[56] References Cited

U.S. PATENT DOCUMENTS

| | | | |
|---|---|---|---|
| 1,726,349 | 8/1929 | Hartsought | 600/11 |
| 2,095,976 | 10/1937 | Foreman | 600/11 |
| 2,753,869 | 7/1956 | Muffly | 600/11 |
| 2,753,870 | 7/1956 | Muffly | 600/11 |
| 2,853,075 | 9/1958 | Hoffman et al. | 600/11 |
| 3,656,481 | 4/1972 | Ness | 600/11 |
| 3,664,327 | 5/1972 | Gordon et al. | 600/11 |
| 3,978,863 | 9/1976 | Fettel et al. | 604/100 |
| 4,790,809 | 12/1988 | Kuntz | 604/8 |
| 4,904,256 | 2/1990 | Yamaguchi | 128/DIG. 25 |
| 5,096,763 | 3/1992 | Ogata et al. | 600/12 |

FOREIGN PATENT DOCUMENTS

| | | | |
|---|---|---|---|
| 0302001 | 2/1989 | European Pat. Off. | 600/11 |
| 0355261 | 2/1990 | European Pat. Off. | 600/11 |
| 2553244 | 5/1977 | Germany | 600/12 |
| 0207333 | 12/1967 | U.S.S.R. | 600/11 |
| 1147411 | 3/1985 | U.S.S.R. | 600/12 |

OTHER PUBLICATIONS

Towbin, R. B., et al. "Magnet Catheter for Removal of Magnetic Foreign Bodies," *American Journal of Roentgenology,* 154:149–150, Jan., 1990.

"FE–EX ™ Orogastric tube–magnet–OGTM–technique: Removal of ingested iron foreign bodies by means of orogastric tube–magnet" Effner, Inc., New York, 1988.

Jaffe, R. B., et al. "Fluoroscopic Removal of Ingested Alkaline Batteries," *Radiology,* 150:585–586, 1984.

Paulson, E. K., et al. "Metallic Foreign Bodies in the Stomach: Fluoroscopic Removal with a Magnetic Orogastric Tube," *Radiology,* 174:191–194, 1990.

Volle, E., et al. "Ingested Foreign Bodies: Removal by Magnet," *Radiology,* 160:407–409, 1986.

*Primary Examiner*—John D. Yasko
*Assistant Examiner*—Manuel Mendez
*Attorney, Agent, or Firm*—Richard J. Godlewski

[57] ABSTRACT

A magnetic retrieval catheter for retrieving a magnetically attractable object such as a disk-shaped battery from the stomach of a patient. The catheter includes an elongated member tube with a neodymium-based rare-earth magnet positioned in the passageway of the tube about the distal end thereof. The elongated member tube comprises a pliable, flexible material such as polyvinylchloride. A compatible polyvinylchloride dispersion coating material surrounds the distal end of the tube and the distal portion of the magnet extending from the passageway of the tube for securing the magnet in the passageway of the tube and for minimizing oxidation of the rare-earth magnet. A handle is attached about the proximal end of the tube for the manipulation of the tube by the physician. A guide is also provided for insertion through the handle and in the tube passageway about the distal end for controlling and advancing the tube.

18 Claims, 1 Drawing Sheet

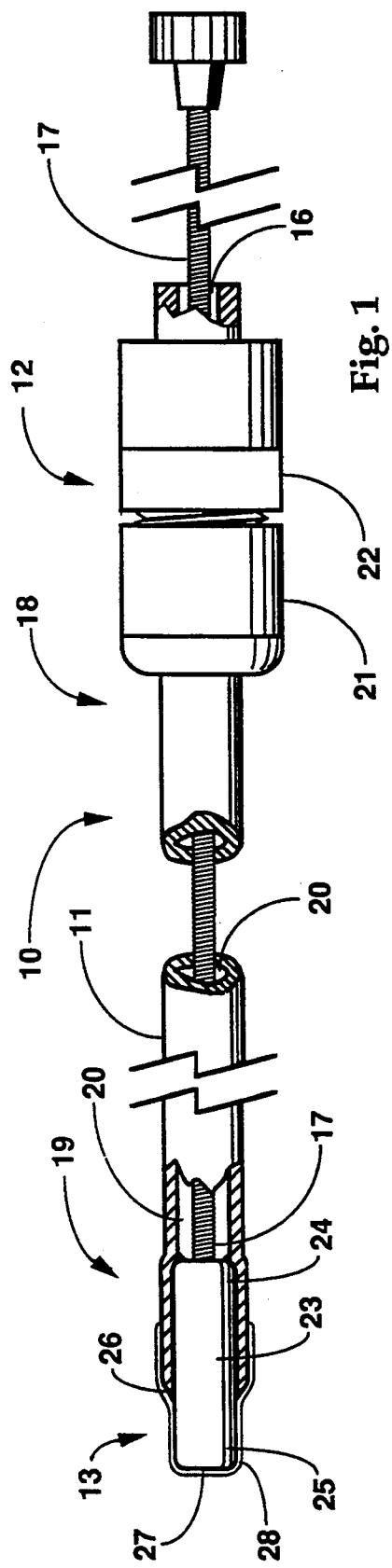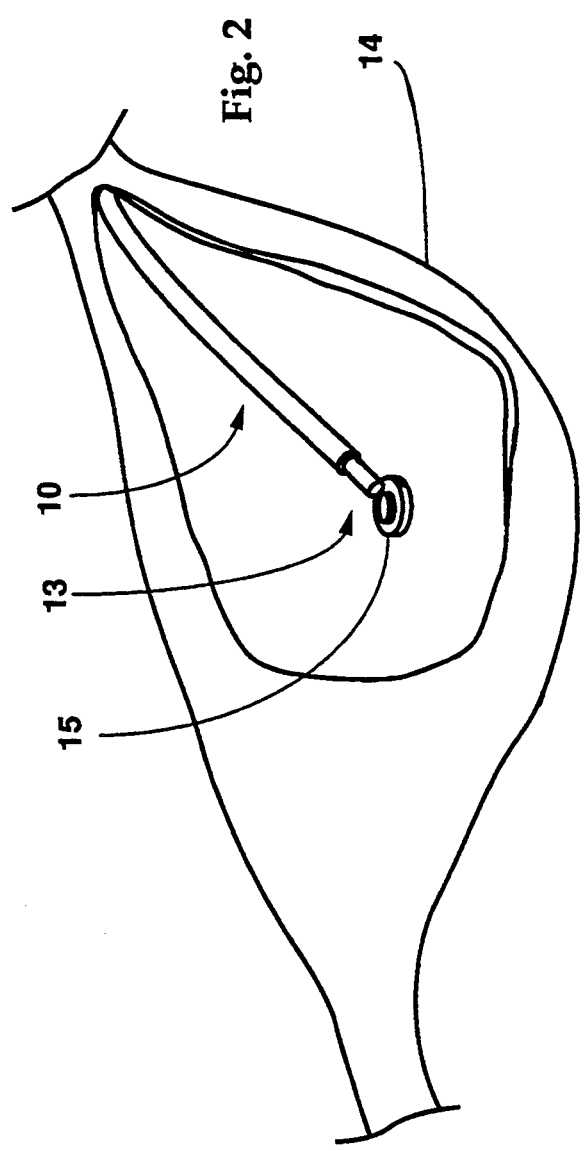

NEODYMIUM-BASED MAGNETIC RETRIEVAL CATHETER

This is a continuation of copending application Ser. No. 07/632,336 filed on Dec. 21, 1990 now abandoned.

TECHNICAL FIELD

This invention relates to catheters and, in particular, to retrieval catheters utilizing a neodymium-based magnet for retrieving a magnetically attractable object from a cavity, duct, or passageway of a patient.

BACKGROUND OF THE INVENTION

Magnetic retrieval catheters have been used for nonsurgical removal of magnetically attractable objects from a cavity, duct, or passageway of a patient. Such catheters have been used, for example, in removing magnetically attractable stents from the bladder through the urethra and in removing accidentally swallowed, magnetically attractable foreign objects such as disk-shaped batteries from the stomach through the esophagus.

When retrieving accidentally swallowed, foreign objects from the stomach, the weight, size, shape, and frictional resistance of the object cannot be accounted for in advance. These problems are heightened when dealing with a small child who has a narrower esophagus and smaller stomach than that of an adult. Accidentally swallowed, magnetically attractable objects range in size and shape from small disk-shaped batteries to large metallic game ball pieces, ball bearings, whistles, and closed pocket knives. Therefore, a magnetic retrieval catheter capable of retrieving large, heavy, or irregularly shaped magnetically attractable objects is preferred. To insure that the magnet of the retrieval catheter will maintain its attachment to a magnetically attractable object, the size and shape of the catheter magnet has been increased. However, large-sized magnets are difficult to ingest and increase the likelihood of trauma to the esophageal passageway.

One prior art retrieval catheter having a large-sized magnet for removing a magnetically attractable object from the stomach has a cylindrical 1.0×1.0 cm magnet within a stainless steel casing. The casing and magnet are attached to the distal end of a 0.3 cm nylon-reinforced polyethylene catheter. As a result, the casing presents an abrupt edge for causing trauma to the esophageal passageway when removing the casing and the attached object from the stomach.

Another problem in removing magnetically attractable objects, particularly prior to the use of rare-earth magnets, is that these objects frequently become dislodged from the magnet during attempted retrieval, especially in the upper esophagus. This has often necessitated the simultaneous use of a second catheter, such as a Foley catheter, with an inflated balloon positioned distally of the object for the removal thereof. The use of two catheters complicates the retrieval procedure. In addition, this complication is heightened in small children, which constitute the largest population of patients.

Still another solution in removing magnetically attractable objects from the stomach is the use of a small-sized rare-earth magnet at the distal end of the catheter to maximize the strength of the magnetic field. However, a problem with such rare-earth magnets is oxidation. These rare-earth magnets oxidize when exposed to corrosive environments such as stomach acid and tend to break apart when so exposed. Furthermore, rare-earth magnets such as samarium-cobalt exhibit magnetic fields of limited strength for removing large, heavy, or irregularly shaped magnetically attractable objects.

SUMMARY OF THE INVENTION

The foregoing problems are solved and a technical advance is achieved in an illustrative neodymium-based magnetic retrieval catheter for removing magnetically attractable objects from a patient. A neodymium-based magnet advantageously presents a high strength magnetic field for maintaining contact with large, heavy, or irregularly shaped magnetically attractable objects. The magnetic retrieval catheter comprises an elongated member having a distal end, a proximal end, and a passageway extending longitudinally therethrough. The neodymium magnet has an elongated body including distal and proximal portions and a maximum cross-sectional dimension that is no greater than that of the elongated member. The proximal portion is positioned in the passageway about the distal end of the elongated member. The distal portion of the magnet extends from the passageway of the elongated member for attracting magnetically attractable objects in, for example, the stomach of a patient. The retrieval catheter further includes a handle positioned about the proximal end of the elongated member for advantageous manipulation and removal of the catheter by the physician. To minimize the problem of oxidation and to further secure the purchase of the magnet within the passageway of the elongated member, the catheter still further comprises a coating material surrounding the distal end of the elongated member and the distal portion of the magnet extending from the passageway.

The elongated member includes a pliable, flexible material tube of, for example, polyvinylchloride. The coating material advantageously comprises a dispersion of, for example, polyvinylchloride, for affixing to the elongated member tube. An adhesive advantageously further secures the proximal portion of the magnet in the passageway of the elongated member tube.

The elongated body of the magnet comprises a uniform cylindrical shape for advantageously enhancing the magnetic field strength at the ends of the magnet. The distal portion of the magnet includes a relatively flat end surface or a blunt distal end for maximizing the contact surface with the object and further enhancing the magnetic field strength of-the magnet. The neodymium-based magnet includes by weight preferably 22 percent neodymium, 2 percent boron, and 70 percent iron.

The catheter also comprises a guide that is insertable in the passageway of the elongated member tube about the distal end thereof for advantageously advancing and controlling the position of the catheter in the esophagus and stomach of the patient. The handle of the catheter includes a passageway sized for insertion of the guide therethrough and into the passageway of the elongated member tube.

BRIEF DESCRIPTION OF THE DRAWING

FIG. 1 depicts a partially sectioned view of the magnetic retrieval catheter of the present invention; and FIG. 2 depicts the distal end of the catheter of FIG. 1 retrieving a disk-shaped battery from the stomach of a patient.

DETAILED DESCRIPTION

Depicted in FIGS. 1 and 2 is an illustrative magnetic retrieval catheter 10 for the nonsurgical removal of a magnetically attractable object such as disk-shaped battery 15 from stomach 14 of a patient. The catheter comprises elongated member tube 11 having proximal end 18, distal end 19, and hollow passageway 20 extending longitudinally therethrough. Handle 12 is attached about the proximal end of the tube for manipulating the catheter. The catheter further comprises neodymium-based magnet 13 having uniform cylindrically shaped body 23 with respective proximal and distal portions 24 and 25. The proximal portion of the magnet is positioned in passageway 20 of the tube with the distal portion of the magnet extending longitudinally from distal end 19 thereof. With the use of a visualization aid such as fluoroscopy, the distal end of the elongated member tube and the magnet are inserted orally through the esophagus and into the stomach of the patient for attaching to and retrieving the magnetically attractable battery. Guide 17, such as a long torque cable available from Cook Inc., Bloomington, Ind., is inserted through the handle and into the passageway of the catheter for assisting the advancement and control of the catheter.

Elongated member tube 11 is approximately 75 cm in length and 18.5 French in diameter with an outside diameter of 0.245" and an inside diameter of 0.179". The tube consists of a pliable, flexible material such as commercially available polyvinylchloride.

Magnet 13 is a neodymium-based rare-earth magnet comprising preferably by weight 70 percent iron, 22 percent neodymium, and 6 percent boron. The magnet is molded and dry-pressed into uniform cylindrically shaped body 23. The magnet is also cintered and heat-treated. The body of the magnet is approximately 7/8" long and ⅜" in diameter and is sized for positioning in and extending from passageway 20 of the elongated member tube. The body has a cross-sectional dimension no larger than that of the elongated member tube. Blunt distal end 27 of the magnet presents a relatively flat end surface for maximizing the surface in contact with the magnetically attractable object. Such a neodymium-based magnet is available from Bunting Magnetics, Inc. of Elk Grove Village, Ill. The energy product level of the magnet, which is indicative of the magnetic field strength, is preferably a grade 27.

Cyanoacrylate-ester adhesive 26, such as commercially available Prism TM 401 adhesive from Loctite Corporation of Newington, Conn., is applied to the proximal portion of the magnet and about the inside distal end of the elongated member tube to fixedly position the proximal portion of the magnet in the passageway of the tube.

Distal portion 25 of the magnet extends approximately 1 cm from distal end 19 of the tube. Coating material 28 surrounds the distal portion and the blunt end of the magnet extending from passageway 20 along with approximately 1 cm of the outer surface of the tube about distal end 19. The coating material protects the distal portion of the magnet from body fluids and oxidation without significantly inhibiting the magnetic strength of the magnet. The coating material comprises a polyvinylchloride dispersion which is commercially available from Schwartz Chemical Company of Long Island City, N.Y. The coating material forms a slick, smooth surface on the elongated member tube about distal end 19 and on distal portion 25 of the magnet. The smooth surface of the coating material eases ingestion and the movement of the magnet in the esophagus. The thickness of the coating is approximately 0.010".

Handle 12 of the catheter comprises well-known 18 French connecting cap 21 and extra large male Luer lock adapter 22 for flaring and securing the proximal end of the tube therein. The flared fitting connection is also secured by the aforementioned cyanoacrylate-ester adhesive. The handle also includes passageway 16 extending longitudinally therethrough and communicating with the longitudinal passageway of the tube. Guide 17 is inserted through the communicating passageways of the handle and tube about the distal end thereof for advancing and controlling the catheter.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. Although the tube and dispersion have been described as being of a polyvinylchloride material, other pliable, flexible materials are also contemplated. The configuration of the handle may also be modified to receive a deflectable tip guide handle. It is further contemplated that the elongated member tube of the catheter may include a side port about the distal end thereof for injecting contrast medium or medications or for irrigating the stomach.

We claim:

1. A magnetic retrieval catheter for retrieving large, heavy, or irregularly shaped magnetically attractable objects, comprising:
    an elongated member having a distal end, a proximal end, and a passageway extending longitudinally therethrough and being totally enclosed about said distal end;
    a handle positioned about said proximal end of said member;
    a neodymium magnet having an elongated body including a distal portion, a proximal portion positioned stationarily in said passageway about said distal end of said member, and a maximum cross-sectional dimension no greater than that of said elongated member, said distal portion of said magnet extending from said passageway about said distal end of said member, said neodymium magnet also having a magnetic field strength that maintains attachment to a large, heavy, or irregularly shaped magnetically attractable object when pulled through a narrow esophagus;
    an adhesive securing said proximal portion of said magnet in said passageway of said member; and
    a nonferrous coating material forming a smooth surface on and surrounding said distal end of said member and said distal portion of said magnet extending from said passageway, said nonferrous coating material minimally affecting said magnetic field strength of said neodymium magnet and protecting said neodymium magnet from oxidation.

2. The catheter of claim 1 wherein said coating material comprises a dispersion.

3. The catheter of claim 2 wherein said dispersion comprises polyvinylchloride.

4. The catheter of claim 1 wherein said elongated member comprises a pliable, flexible material tube.

5. The catheter of claim 4 wherein said tube comprises polyvinylchloride.

6. The catheter of claim 1 further comprising a guide insertable in said passageway to said magnet.

7. The catheter of claim 6 wherein said handle includes a passageway sized for insertion of said guide therethrough.

8. The catheter of claim 1 wherein said elongated body of said magnet has a uniform cylindrical shape.

9. The catheter of claim 1 wherein said distal portion of said magnet includes a relatively flat end surface that maximizes said magnetic field strength of said magnet thereat.

10. The catheter of claim 1 wherein said distal portion of said magnet includes a blunt distal end that maximizes said magnetic field strength of said magnet thereat.

11. The catheter of claim 1 wherein said neodymium magnet further includes boron.

12. The catheter of claim 11 wherein said magnet still further includes iron.

13. A catheter for retrieving a large, heavy, or irregularly shaped magnetically attractable object from a patient, comprising:

a pliable, flexible material tube having a distal end, a proximal end, and a passageway extending longitudinally therethrough and being totally enclosed about said distal end;

a handle positioned about said proximal end of said tube;

a neodymium magnet having an elongated body including a distal portion, a proximal portion positioned stationarily in said passageway about said distal end of said tube, and a maximum cross-sectional dimension no greater than that of said tube, said distal portion of said magnet extending from said passageway about said distal end of said tube, said neodymium magnet also having a magnetic field strength that maintains attachment to a large, heavy, or irregularly shaped magnetically attractable object when pulled through a narrow esophagus;

a nonferrous coating material forming a smooth surface on and surrounding said distal end of said tube and said distal portion of said magnet extending from said passageway, said nonferrous coating material minimally affecting said magnetic field strength of said neodymium magnet and protecting said neodymium magnet from oxidation;

an adhesive securing said proximal portion of said magnet in said passageway of said tube; and a guide insertable in said passageway through said proximal end of said tube to said magnet.

14. The catheter of claim 13 wherein said tube comprises polyvinylchloride and wherein said coating material comprises a polyvinychloride dispersion.

15. The catheter of claim 14 wherein said elongated body of said magnet has a uniform cylindrical shape.

16. The catheter of claim 15 wherein said distal portion of said magnet includes a relatively flat end surface that maximizes said magnetic field strength of said magnet thereat.

17. The catheter of claim 13 wherein said magnet includes boron and iron.

18. A catheter for retrieving a large, heavy, or irregularly shaped magnetically attractable object from a patient, comprising:

a polyvinylchloride material tube having a distal end, a proximal end, and a first passageway extending longitudinally therethrough and being totally enclosed about said distal end;

a handle positioned about said proximal end of said tube and having a second passageway extending therethrough and communicating with said first passageway;

a rare-earth magnet including by weight 22 percent neodymium, 2 percent boron, and 70 percent iron and having a uniform cylindrical body including a distal portion having a relatively flat end surface, a proximal portion positioned stationarily in said passageway about said distal end of said tube, and a maximum cross-sectional dimension no greater than that of said tube, said distal portion of said magnet extending from said passageway about said first end of said tube, said rare-earth magnet also having a magnetic field strength that maintains attachment to a large, heavy, or irregularly shaped magnetically attractable object when pulled through a narrow esophagus, said flat end surface maximizing said magnetic field strength of said magnet thereat;

a polyvinylchloride dispersion coating material forming a smooth surface on and surrounding said distal end of said tube and said distal portion of said magnet extending from said passageway, said polyvinylchloride dispersion coating material minimally affecting said magnetic field strength of said magnet and protecting said magnet from oxidation;

an adhesive securing said proximal portion of said magnet in said passageway of said tube; and a guide insertable through said first and second passageways about said distal end of said tube.

* * * * *